(12) United States Patent
Medintz et al.

(10) Patent No.: US 9,139,614 B2
(45) Date of Patent: Sep. 22, 2015

(54) MODULAR LINKERS FOR CONJUGATION OF ORGANIC SUBSTANCES TO SUBSTANTIALLY INORGANIC SUBSTANCES AND METHODS OF MANUFACTURE AND USE THEREOF

(75) Inventors: Igor L. Medintz, Springfield, VA (US); Lorenzo Berti, Bologna (IT); Paolo Facci, Genoa (IT); Hedi M. Mattoussi, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 820 days.

(21) Appl. No.: 11/739,969

(22) Filed: Apr. 25, 2007

(65) Prior Publication Data
US 2009/0159842 A1 Jun. 25, 2009

(51) Int. Cl.
*A61K 38/00* (2006.01)
*C07K 7/06* (2006.01)

(52) U.S. Cl.
CPC ........................................ *C07K 7/06* (2013.01)

(58) Field of Classification Search
USPC .......... 252/182.12; 435/6; 436/525; 530/323; 536/23.1
See application file for complete search history.

(56) References Cited

U.S. PATENT DOCUMENTS

| | | | |
|---|---|---|---|
| 7,524,925 B2 * | 4/2009 | Bruce et al. .................... | 530/300 |
| 2005/0130167 A1 | 6/2005 | Bao et al. | |
| 2006/0068506 A1 * | 3/2006 | Uyeda et al. .................. | 436/525 |

FOREIGN PATENT DOCUMENTS

WO 2006096185 9/2006

OTHER PUBLICATIONS

Search Report and Written Opinion in PCT/US2008/063591.
Abad, et al., "Functionalization of Thioctic Acid-Capped Gold Nanoparticles for Specific Immobilization of Histidine-Tagged Proteins," J. Am. Chem. Soc., (2005) 127, 5689-5694.
Alivisatos, et al., "Quantum dots as cellular probes," Annu. Rev. Biomed. Eng., (2005) 7, 55-76.
Blum, et al., "Templated self-assembly of quantum dots from aqueous solution using protein scaffolds," Nanotechnology, (Sep. 22, 2006) 17, 5073-5079.
Burda, et al., "Chemistry and properties of nanocrystals of different shapes," Chem Rev., (Mar. 18, 2005) 105, 1025-102.
Clapp, et al., "Forster resonance energy transfer investigations using quantum-dot fluorophores," Chemphyschem., (Dec. 21, 2005) 16, 47-57.

(Continued)

*Primary Examiner* — Monique Peets
(74) *Attorney, Agent, or Firm* — US Naval Research Laboratory; Joseph T. Grunkemeyer

(57) ABSTRACT

A modular linker includes an inorganic binding entity having an affinity for a substantially inorganic substance, and an organic binding entity capable of binding with an organic substance covalently bonded thereto. The modular linker is capable of being stored in a stable condition for later use. The modular linker may be synthesized by modifying the inorganic binding entity to be covalently bonded to an organic binding entity and storing the modular linker in an inert environment from about a day up to at least 1 week. The modular linker may be conjugated to an organic substance and to a substantially inorganic substance in substantially a 1:1 ratio. The modular linker may have more than one organic binding entity covalently bonded to an inorganic binding entity or vice-versa. Also, a particular modular linker may have an organic binding entity capable of binding with a nucleic acid sequence.

26 Claims, 7 Drawing Sheets

(56) References Cited

OTHER PUBLICATIONS

Clapp, et al., "Fluorescence resonance energy transfer between quantum dot donors and dye-labeled protein acceptors," J. Am. Chem. Soc., (2004) 126, 301-10.

Dawson, et al., "Synthesis of native proteins by chemical ligation," Ann. Rev. Biochem., (2000) 69, 923-960.

de la Garza, et al., "Surface States of Titanium Dioxide Nanoparticles Modified with Enediol Ligands," J. Phys. Chem. B, (2006) 110, 680-686.

Delehanty, et al., "Self-Assembled Quantum Dot-Peptide Bioconjugates for Selective Intracellular Delivery," Bioconjugate Chem., (2006), 17, 920-927.

Gerion, et al., "Synthesis and properties of biocompatible water-soluble silicacoated CdSe/ZnS semiconductor quantum dots," J. Phys. Chem. B, (Jun. 5, 2001) 105 (37), 8861-8871.

Goldman, et al., "Self-assembled luminescent CdSe-ZnS quantum dot bioconjugates prepared using engineered poly-histidine terminated proteins," Anal. Chim. Acta, (May 25, 2004), 534, 63-67.

Goldman, et al., "Bioconjugates of luminescent CdSe-ZnS quantum dots with engineered recombinant proteins: Novel self-assembled tools for biosensing," Mat. Res. Soc. Symp., (2001) 642, J2.8.1-6.

Hainfeld, et al., "Ni-NTA-gold clusters target His-tagged proteins," J. Struct. Biol., (1999) 127, 185-198.

Hermanson, Bioconjugate Techniques, Academic Press, (Jan. 15, 1996), pp. 140 and 173.

Katz, et al., "Integrated nanoparticle-biomolecule hybrid systems: synthesis, properties, and applications," Angew Chem. Int. Ed., (2004) 43, 6042-108.

Love, et al., "Self-assembled monolayers of thiolates on metals as a form of nanotechnology," Chem. Rev., (Mar. 25, 2005) 105, 1103-69.

Mao, et al., "Virus-based toolkit for the directed synthesis of magnetic and semiconducting nanowires," Science, (Jan. 9, 2004) 303, 213-7.

Medintz, et al., "A fluorescence resonance energy transfer-derived structure of a quantum dot-protein bioconjugate nanoassembly," PNAS (Jun. 21, 2004) 101(26), 9612-9617.

Medintz, et al., "Quantum dot bioconjugates for imaging, labelling and sensing," Nat. Mater., (Jun. 2005) 4, 435-446.

Michalet, et al., "Quantum dots for live cells, in vivo imaging, and diagnostics," Science, (Jan. 28, 2005) 307, 538-44.

Min, et al., "Immobilized metal affinity chromatography of DNA," Nucleic Acids Research, (1996) 24(19), 3806-3810.

Sapsford, et al., "Materials for Fluorescence Resonance Energy Transfer Analysis: Beyond Traditional Donor-Acceptor Combinations," Agnew. Chem. Int. Ed., (2006) 45, 4562-4588.

Sarikaya, et al., "Molecular biomimetics: nanotechnology through biology," Nat. Mater., (Sep. 2003) 2, 577-85.

Thodima, et al., "RiboaptDB: A Comprehensive database of ribozymes and aptamers," BMC Bioinformatics: 7, No. S6, Supp. 2 (Sep. 26, 2006).

Ueda, et al., "Current and prospective applications of metal ion-protein binding." J. Chrom A., (2003) 988, 1-23.

You, et al., "Aptamers as functional nucleic acids: In vitro selection and biotechnological applications," Biotechnology and Bioprocess Engineering, (Mar.-Apr. 2003) 8(2), 64-75.

\* cited by examiner

SEQUENCE LISTING

```
<160> NUMBER OF SEQ ID NOS: 28

<210> SEQ ID NO 1
<211> LENGTH: 14
<212> TYPE: PRT
<213> ORGANISM: Artificial
<220> FEATURE:
<223> OTHER INFORMATION: Synthesized sequence

<400> SEQUENCE: 1

Met His Gly Lys Thr Gln Ala Thr Ser Gly Thr Ile Gln Ser
1               5                   10

<210> SEQ ID NO 2
<211> LENGTH: 21
<212> TYPE: PRT
<213> ORGANISM: Artificial
<220> FEATURE:
<223> OTHER INFORMATION: Synthesized sequence

<400> SEQUENCE: 2
```

```
Ser Lys Thr Ser Leu Gly Gln Ser Gly Ala Ser Leu Gln Gly Ser Glu
1               5                   10                  15

Lys Leu Thr Asn Gly
            20

<210> SEQ ID NO 3
<211> LENGTH: 21
<212> TYPE: PRT
<213> ORGANISM: Artificial
<220> FEATURE:
<223> OTHER INFORMATION: Synthesized sequence

<400> SEQUENCE: 3

Gln Ala Thr Ser Glu Lys Leu Val Arg Gly Met Glu Gly Ala Ser Leu
1               5                   10                  15

His Pro Ala Lys Thr
            20

<210> SEQ ID NO 4
<211> LENGTH: 7
<212> TYPE: PRT
<213> ORGANISM: Artificial
<220> FEATURE:
<223> OTHER INFORMATION: Synthesized sequence

<400> SEQUENCE: 4

Asp Arg Thr Ser Thr Trp Arg
1               5

<210> SEQ ID NO 5
<211> LENGTH: 7
<212> TYPE: PRT
<213> ORGANISM: Artificial
<220> FEATURE:
<223> OTHER INFORMATION: Synthesized seqeunce

<400> SEQUENCE: 5

Gln Ser Val Thr Ser Thr Lys
1               5

<210> SEQ ID NO 6
<211> LENGTH: 7
<212> TYPE: PRT
<213> ORGANISM: Artificial
<220> FEATURE:
<223> OTHER INFORMATION: Synthesized seqence

<400> SEQUENCE: 6

Ser Ser Ser His Leu Asn Lys
1               5

<210> SEQ ID NO 7
<211> LENGTH: 7
<212> TYPE: PRT
<213> ORGANISM: Artificial
<220> FEATURE:
<223> OTHER INFORMATION: Synthesized seqence

<400> SEQUENCE: 7

Ser Val Thr Gln Asn Lys Tyr
1               5

<210> SEQ ID NO 8
<211> LENGTH: 7
<212> TYPE: PRT
```

```
<213> ORGANISM: Artificial
<220> FEATURE:
<223> OTHER INFORMATION: Synthesized sequence

<400> SEQUENCE: 8

Ser Pro His Pro Gly Pro Tyr
1               5

<210> SEQ ID NO 9
<211> LENGTH: 7
<212> TYPE: PRT
<213> ORGANISM: Artificial
<220> FEATURE:
<223> OTHER INFORMATION: Synthesized sequence

<400> SEQUENCE: 9

His Ala Pro Thr Pro Met Leu
1               5

<210> SEQ ID NO 10
<211> LENGTH: 12
<212> TYPE: PRT
<213> ORGANISM: Artificial
<220> FEATURE:
<223> OTHER INFORMATION: Synthesized sequence

<400> SEQUENCE: 10

Ala Tyr Ser Ser Gly Ala Pro Pro Met Pro Pro Phe
1               5                   10

<210> SEQ ID NO 11
<211> LENGTH: 12
<212> TYPE: PRT
<213> ORGANISM: Artificial
<220> FEATURE:
<223> OTHER INFORMATION: Synthesized sequence

<400> SEQUENCE: 11

Asn Pro Ser Ser Leu Phe Arg Tyr Leu Pro Ser Asp
1               5                   10

<210> SEQ ID NO 12
<211> LENGTH: 12
<212> TYPE: PRT
<213> ORGANISM: Artificial
<220> FEATURE:
<223> OTHER INFORMATION: Synthesized sequence

<400> SEQUENCE: 12

Ser Leu Ala Thr Gln Pro Pro Arg Thr Pro Pro Val
1               5                   10

<210> SEQ ID NO 13
<211> LENGTH: 12
<212> TYPE: PRT
<213> ORGANISM: Artificial
<220> FEATURE:
<223> OTHER INFORMATION: Synthesized sequence

<400> SEQUENCE: 13

Met Ser Pro His Pro His Pro Arg His His His Thr
1               5                   10

<210> SEQ ID NO 14
<211> LENGTH: 12
<212> TYPE: PRT
<213> ORGANISM: Artificial
```

```
<220> FEATURE:
<223> OTHER INFORMATION: Synthesized sequence

<400> SEQUENCE: 14

Arg Gly Arg Arg Arg Arg Leu Ser Cys Arg Leu Leu
1               5                   10

<210> SEQ ID NO 15
<211> LENGTH: 12
<212> TYPE: PRT
<213> ORGANISM: Artificial
<220> FEATURE:
<223> OTHER INFORMATION: Synthesized sequence

<400> SEQUENCE: 15

Lys Pro Ser His His His His His Thr Gly Ala Asn
1               5                   10

<210> SEQ ID NO 16
<211> LENGTH: 21
<212> TYPE: PRT
<213> ORGANISM: Artificial
<220> FEATURE:
<223> OTHER INFORMATION: Synthesized sequence

<400> SEQUENCE: 16

Val Lys Thr Gln Ala Thr Ser Arg Glu Glu Pro Pro Arg Leu Pro Ser
1               5                   10                  15

Lys His Arg Pro Gly
            20

<210> SEQ ID NO 17
<211> LENGTH: 14
<212> TYPE: PRT
<213> ORGANISM: Artificial
<220> FEATURE:
<223> OTHER INFORMATION: Synthesized sequence

<400> SEQUENCE: 17

Met Asp His Gly Lys Tyr Arg Gln Lys Gln Ala Thr Pro Gly
1               5                   10

<210> SEQ ID NO 18
<211> LENGTH: 20
<212> TYPE: PRT
<213> ORGANISM: Artificial
<220> FEATURE:
<223> OTHER INFORMATION: Synthesized sequence

<400> SEQUENCE: 18

Asn Thr Arg Met Thr Ala Arg Gln His Arg Ser Ala Asn His Lys Ser
1               5                   10                  15

Thr Gln Arg Ala
            20

<210> SEQ ID NO 19
<211> LENGTH: 9
<212> TYPE: PRT
<213> ORGANISM: Artificial
<220> FEATURE:
<223> OTHER INFORMATION: Synthesized sequence

<400> SEQUENCE: 19

Tyr Asp Ser Arg Ser Met Arg Pro His
1               5
```

<210> SEQ ID NO 20
<211> LENGTH: 12
<212> TYPE: PRT
<213> ORGANISM: Artificial
<220> FEATURE:
<223> OTHER INFORMATION: Synthesized sequence

<400> SEQUENCE: 20

His Thr Gln Asn Met Arg Met Tyr Glu Pro Trp Phe
1               5                   10

<210> SEQ ID NO 21
<211> LENGTH: 12
<212> TYPE: PRT
<213> ORGANISM: Artificial
<220> FEATURE:
<223> OTHER INFORMATION: Synthesized sequence

<400> SEQUENCE: 21

Asp Val Phe Ser Ser Phe Asn Leu Lys His Met Arg
1               5                   10

<210> SEQ ID NO 22
<211> LENGTH: 9
<212> TYPE: PRT
<213> ORGANISM: Artificial
<220> FEATURE:
<223> OTHER INFORMATION: Synthesized sequence

<400> SEQUENCE: 22

Val Val Arg Pro Lys Ala Ala Thr Asn
1               5

<210> SEQ ID NO 23
<211> LENGTH: 9
<212> TYPE: PRT
<213> ORGANISM: Artificial
<220> FEATURE:
<223> OTHER INFORMATION: Synthesized sequence

<400> SEQUENCE: 23

Arg Ile Arg His Arg Leu Val Gly Gln
1               5

<210> SEQ ID NO 24
<211> LENGTH: 9
<212> TYPE: PRT
<213> ORGANISM: Artificial
<220> FEATURE:
<223> OTHER INFORMATION: Synthesized sequence

<400> SEQUENCE: 24

Arg Arg Thr Val Lys His His Val Asn
1               5

<210> SEQ ID NO 25
<211> LENGTH: 12
<212> TYPE: PRT
<213> ORGANISM: Artificial
<220> FEATURE:
<223> OTHER INFORMATION: Synthesized sequence

<400> SEQUENCE: 25

Ala Gln Asn Pro Ser Asp Asn Asn Thr His Thr His
1               5                   10

```
-continued

<210> SEQ ID NO 26
<211> LENGTH: 12
<212> TYPE: PRT
<213> ORGANISM: Artificial
<220> FEATURE:
<223> OTHER INFORMATION: Synthesized sequence

<400> SEQUENCE: 26

Arg Leu Glu Leu Ala Ile Pro Leu Gln Gly Ser Gly
1               5                   10

<210> SEQ ID NO 27
<211> LENGTH: 12
<212> TYPE: PRT
<213> ORGANISM: Artificial
<220> FEATURE:
<223> OTHER INFORMATION: Synthesized sequence

<400> SEQUENCE: 27

Thr Pro Pro Arg Pro Ile Gln Tyr Asn His Thr Ser
1               5                   10

<210> SEQ ID NO 28
<211> LENGTH: 7
<212> TYPE: PRT
<213> ORGANISM: Artificial
<220> FEATURE:
<223> OTHER INFORMATION: Synthesized sequence

<400> SEQUENCE: 28

Asn Asn Pro Met His Gln Asn
1               5
```

MODULAR LINKERS FOR CONJUGATION OF ORGANIC SUBSTANCES TO SUBSTANTIALLY INORGANIC SUBSTANCES AND METHODS OF MANUFACTURE AND USE THEREOF

FIELD OF THE INVENTION

The present invention is generally directed to one or more modular linkers, particularly stable and storable modular linkers, for conjugation of an organic substance to a substantially inorganic substance, a method of synthesizing a modular linker and a method of conjugating the organic substance and the substantially inorganic substance.

BACKGROUND OF THE INVENTION

Many entities are known for having an affinity for certain inorganic substances. This interaction has been exploited primarily for the purification of appropriately appended recombinant proteins from various growth and other media and a variety of such media and purification protocols are commercially available. For example, a variety of peptidyl sequences are know to have an affinity for inorganic surfaces. Histidine terminated peptide sequences, in particular poly-histidine sequences, are known to have an affinity for certain nanoparticles, such as CdSe/ZnS nanoparticles and quantum dots (QDs). Poly-cysteine residues have been introduced into proteins and peptides recombinantly to facilitate their binding to gold and other nanoparticles and surfaces. Several unique peptide sequences have been selected for their binding to various metal and/or semiconductor surfaces using phage display and other selection/molecular evolution techniques. As non-limiting examples, Table I below illustrates a variety of peptide sequences and the particular inorganic materials for which they are know to have an affinity.

Nanocrystals and QDs are generally composed of metals, metal oxides and semiconductors, all substantially inorganic materials. Nanoparticles and QDs display unique spectroscopic and electronic properties distinct from molecular compounds or parent bulk materials. QDs have been widely demonstrated as useful tools and probes for the development of highly sensitive biological and other types of multiplexing assays, i.e. the simultaneous detection of multiple signals. The substantially inorganic nature of QDs and nanoparticles makes it difficult to conjugate them to organic substances by standard methodologies. As such, there are only limited methods available for coupling nanoparticles and QDs to organic substances, such as proteins or peptides (or any biomolecule), many of which result in a heterogeneous composite structures or aggregates. These concerns continue to hinder progress in this field.

Current methods for linking organic substances to QDs involve multiple steps, are cumbersome and not practical. As a result, current methods for linking organic substances and inorganic substances are only suitable for very specific conjugation applications. While specific chemistries may have been developed to join a particular organic substance to a particular inorganic substance, the process for doing so is often very complex, can take several days to proceed and may not be applicable to other organic or inorganic substances pairs. For example, biomolecule attachment to a functionalized QD is usually achieved by employing a large excess of the biomolecule, frequently resulting in a QD to biomolecule ratio that cannot be controlled, cross reactivity, aggregation and precipitation. As such, the aggregated size of the final QD-biomolecule conjugate may be too large so as to preclude certain applications. Further, the chemistries and methods used to link inorganic substances to organic substances are generally unstable reactions, requiring the immediate conjugation of the organic substance and/or inorganic substance

TABLE I

| Peptidyl sequences | Inorganic material for which there is an affinity |
|---|---|
| MHGKTQATSGTIQS (SEQ ID NO 1) | Gold |
| SKTSLGQSGASLQGSEKLTNG (SEQ ID NO 2) | |
| QATSEKLVRGMEGASLHPAKT (SEQ ID NO 3) | |
| DRTSTWR (SEQ ID NO 4) | Platinum |
| QSVTSTK (SEQ ID NO 5) | |
| SSSHLNK (SEQ ID NO 6) | |
| SVTQNKY (SEQ ID NO 7) | Palladium |
| SPHPGPY (SEQ ID NO 8) | |
| HAPTPML (SEQ ID NO 9) | |
| AYSSGAPPMPPF (SEQ ID NO 10) | Silver |
| NPSSLFRYLPSD (SEQ ID NO 11) | |
| SLATQPPRTPPV (SEQ ID NO 12) | |
| MSPHPHPRHHHT (SEQ ID NO 13) | Silicon oxide |
| RGRRRRLSCRLL (SEQ ID NO 14) | |
| KPSHHHHHTGAN (SEQ ID NO 15) | |
| VKTQATSREEPPRLPSKHRPG (SEQ ID NO 16) | Zeolites |
| MDHGKYRQKQATPG (SEQ ID NO 17) | |
| NTRMTARQHRSANHKSTQRA (SEQ ID NO 18) | Zinc oxide |
| YDSRSMRPH (SEQ ID NO 19) | |
| HTQNMRMYEPWF (SEQ ID NO 20) | Calcium carbonate |
| DVFSSFNLKHMR (SEQ ID NO 21) | |
| VVRPKAATN (SEQ ID NO 22) | Chromium oxide |
| RIRHRLVGQ (SEQ ID NO 23) | |
| RRTVKHHVN (SEQ ID NO 24) | Iron oxide |
| AQNPSDNNTHTH (SEQ ID NO 25) | Gallium arsenide |
| RLELAIPLQGSG (SEQ ID NO 26) | |
| TPPRPIQYNHTS (SEQ ID NO 27) | |
| NNPMHQN (SEQ ID NO 28) | Zinc sulfide |

See M. Sarikaya, et al. "Molecular biomimetics: nanotechnology through biology," Nature Materials, Vol. 2, pp. 577-585 (September 2003), which is incorporated herein by reference in its entirety.

without degrading of the intermediate linker. Further, the actual conjugation steps often require several subsequent purification steps, making the process of conjugation selective to the particular protein, complex and burdensome.

BRIEF SUMMARY OF THE INVENTION

Research in this area will be greatly enhanced, perhaps may even become routine with the availability of stable and storable modular linkers readily available to react with particular substantially inorganic substances and particular organic substances in a controllable and predictable manner. Thus, the present application is generally directed to a modular linker for the simple conjugation of a substantially inorganic substance and an organic substance and a method for its synthesis and use. The modular linker is preferably stable and storable for a substantial period of time, such that it may be available for the immediate and controlled conjugation of a substantially inorganic substance and an organic substance. For example, a variety of modular linkers may be manufactured in advance of a desired application, made commercially available, such as in a kit, and shipped to a laboratory where they can be stored until the particular linker is needed.

Further conjugation of a substantially inorganic substance with an organic substance can be achieved via the modular linker in a controlled manner to create a ratio of substantially inorganic substance to an organic substance of about 1:1. As such, excess organic substances and inorganic substances are not needed to ensure good reaction yields. Also, the risk of having aggregation and cross-reactivity is significantly decreased.

Thus, an embodiment of the present invention includes a modular linker including an inorganic binding entity having an affinity for a substantially inorganic substance and an organic binding entity capable of binding with an organic substance, wherein the organic binding entity is covalently bonded to the inorganic binding entity. In a particular embodiment of the present invention, the modular linker is capable of being stored in a stable condition for later use.

An embodiment of the present invention is a method for synthesizing a stable modular linker that includes providing an inorganic binding entity having an affinity for a substantially inorganic substance, modifying the inorganic binding entity to be covalently bonded to an organic binding entity to form a modular linker and storing the modular linker in an inert environment for at least 1 week.

Another embodiment of the present invention is a method for linking a substantially inorganic substance to one or more organic substances that includes providing a modular linker having an inorganic binding entity having an affinity for the substantially inorganic substance and an organic binding entity capable of reacting with at least one organic substance that is covalently bonded to the inorganic binding entity. The method also includes conjugating the modular linker to one or more organic substances by reacting the modular linker with at least one organic substance in substantially a 1:1 ratio and conjugating the modular linker to a substantially inorganic substance by introducing the modular linker to the substantially inorganic substance in a suitable buffer in substantially a 1:1 ratio.

Another embodiment of the present invention is a modular linker that includes an inorganic binding entity having an affinity for a substantially inorganic substance, a first organic binding entity capable of binding with a first organic substance and a second organic binding entity capable of binding with a second organic substance that is different from the first organic substance. In this modular linker, the first and second organic binding entities are covalently bonded to the inorganic binding entity.

Another embodiment of the present invention is a modular linker that includes a first inorganic binding entity having an affinity for a first substantially inorganic substance, a second inorganic binding entity having an affinity for a second substantially inorganic substance that is different from the first substantially inorganic substance and an organic binding entity capable of binding with an organic substance. In this embodiment, the first and second inorganic binding entities are covalently bonded to the organic binding entity.

Another embodiment of the present invention is a modular linker that includes an inorganic binding entity having an affinity for a substantially inorganic substance and an organic binding entity capable of binding particularly with a nucleic acid sequence, wherein the organic binding entity is covalently bonded to the inorganic binding entity.

The foregoing and other features, advantages and embodiments of the present invention will be apparent from the following, more particular description of a preferred embodiment of the invention, as illustrated in the accompanying drawings.

DETAILED DESCRIPTION OF THE INVENTION

Figure 1:
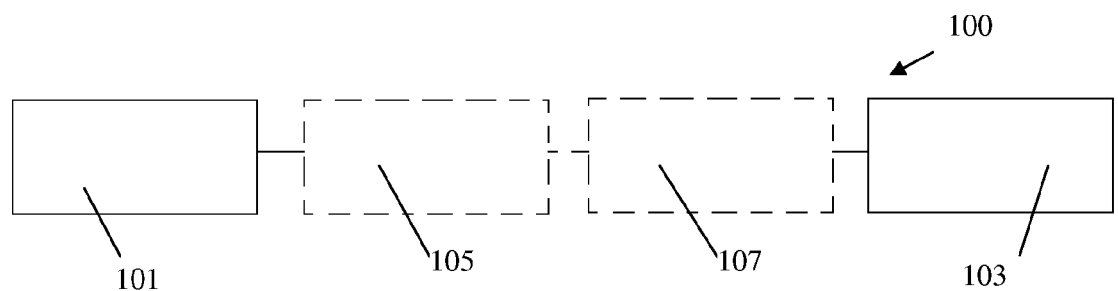
FIG. 1 is a schematic of an example of a modular linker of the present invention, using black boxes to demonstrate the modularity of the linker.

Preferred embodiments of the present invention are now described with reference to the Figures, in which like reference numerals are generally used to indicate identical or functionally similar elements. The following description uses chemistry and terminology common to synthetic peptide chemistry, and thus the full implication of this disclosure should be apparent to one skilled in the art. In the Figures, the left most digit of each reference numeral generally corresponds to the Figure in which the reference numeral first appears. While specific details of the preferred embodiments are discussed, it should be understood that this is done for illustrative purposes only. A person skilled in the relevant art will recognize that other configurations and arrangements can be used without departing from the spirit and scope of the invention. It will also be apparent to a person skilled in the relevant art that this invention can also be employed in other applications.

The present invention is generally directed to modular linkers for binding molecules together that do not have a natural binding affinity. In particular, the modular linkers are designed to link organic substances to various substantially inorganic substances, including but not limited to metals, metal oxides, semiconductors, nanoparticles, nanocrystals, quantum dots and other inorganic surfaces or particles. A particular example of substantially inorganic substances is nanocrystals or QDs having a cadmium selenide (CdSe) core and a zinc sulphide (ZnS) shell. The organic substances are preferably biomolecules, including but not limited to peptides, proteins, nucleotides enzymes, antibodies, carbohydrates, sugars, lipids and other biomolecular agents.

The modularity of the linkers is due to the fact that the linkers include two distinct modular entities that can be arranged or fitted together in a variety of ways, one or more of which maybe reactive, i.e., in a state that will easily chemically react with a designated organic substance (for example, without the need for further reagents) and/or substantially inorganic substance for easy application of the modular linkers.

FIG. 1 is a schematic of an example of a modular linker 100 of the present invention. At the very least, modular linker 100 includes an inorganic binding entity 101 and an organic binding entity 103, which may be disposed on an opposite end of the modular linker 100 from the inorganic binding entity 101. Inorganic binding entity 101 may be any entity known to bind to a substantially inorganic substance.

For example, the inorganic binding entity may be, but need not be limited to, a poly-histidine sequence, poly-cysteine residues or another unique peptidyl sequences known to have an affinity for substantially inorganic substances, such as those provided in Table I, above. Alternatively, any other entity known to have an affinity for inorganic substances other than peptidyl sequences may be suitable as the inorganic binding entity. For example, certain nucleic acid sequence aptamers can be chemically modified to have an affinity for small inorganic chemical compounds, described in an article by K. M, You et al., *Biotechnology and BioProcess Engineering*, 8(2), pp 64-75 (March-April 2003), which is incorporated by reference herein in its entirety. Dopamine has shown an affinity for titanium oxide nanoparticles. Thiol-modified molecules have shown affinity for gold nanoparticles. Also, certain chemical reactive groups are known to have an affinity for inorganic surfaces. For example, a DNA strand with a tag consisting of six successive 6-histaminylpurine residues has shown an affinity for nickel metal surfaces, without requiring a polypeptidyl sequences.

Similarly, organic binding entity 103 may be any entity known to bind to, react with or otherwise have an affinity for organic substances, particularly biomolecules. For example, the organic binding entity may be, but is not limited to, any of the functionally reactive chemical groups provided below in Table II. Additional examples of organic binding entities include but are not limited to a functional chemical group selective to a particular region of a biomolecule, an aptamer selective to a specific protein, a biotin selective to avidin, a glucose molecule selective to a glucose binding protein, a sugar selective to lectin, an antigen or hapten selective to a particular antibody, an antibody selective to a particular antigen or hapten, p-benzylguanine modified group selective to DNA alkyl transferase, glutathione selective to glutathione-s-transferase, and a nucleotide sequence selective to a complementary nucleotide sequence.

Optional entities 105 and 107 may be optionally further introduced into the modular linker. One or more optional entities 105 and 107 may be, for example, a spacer that might be introduced between inorganic binding entity 101 and organic binding entity 103 in order to optimize the spatial arrangement between a substantially inorganic substance and a biomolecule. Examples of spacers include, but are not limited to, a peptidyl alpha helix, a peptidyl beta strand, a nucleotide sequence, alkane chains or chemical polymers of a predetermined length.

Alternatively, one or more optional entities 105 and 107 may be a solubility entity provided to modulate the solubility of the modular linker in different environments. Examples of solubility entities include, but are not limited to, hydroxylated compounds, sugars, charged peptidyl residues or sulfonated chemical groups. In yet another embodiment, one or more optional entities 105 and 107 may be additional organic binding entities and/or additional inorganic binding entities that may be used to introduce further attachment points for further linking to subsequent and/or alternative binding regions of the same or different organic substances and/or substantially inorganic substances.

Figure 2:
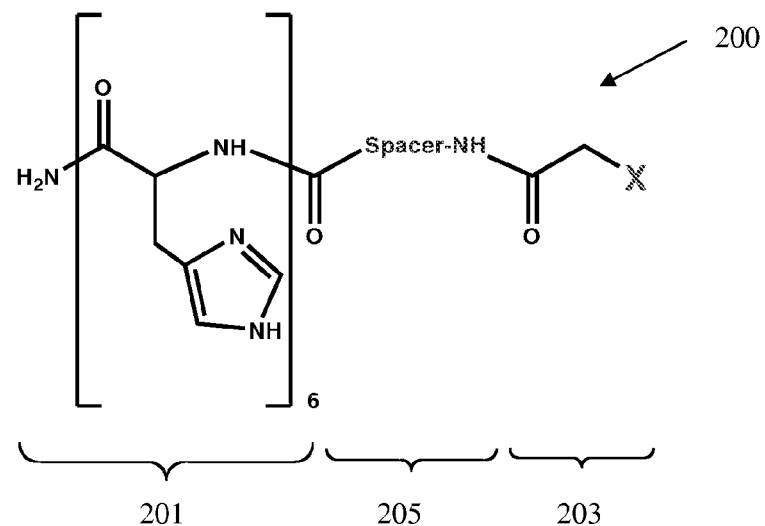
FIG. 2 is a schematic representation of an example of a functional linker of the present invention.

The examples provided herein demonstrate some, but not all, of the different functions that can be imparted to modular linkers 100 by changing the inorganic binding entity 101, organic binding entity 105 or one or more of the optional entities 105 and 107, each of which may be selected as desired, highlighting the modularity of this approach. In alternative embodiments, there also may be greater or fewer optional entities 105 and 107 and/or optional entities 105 and 107 may be conjugated with one or both of the inorganic binding entity 101 and organic binding entity 103 rather than disposed therebetween, depending upon the particular application desired for the modular linker 100. For example, FIG. 2 provides an example of a linker where only one spacer is provided between an inorganic binding entity and an organic binding entity.

Thus, the modular linkers of the present invention have the ability to bind to both substantially inorganic substances and to concurrently bind to targeted organic substances, such as particular biomolecules. The modular linker has a modular design such that specific properties can be introduced during synthesis of the linkers as desired for a particular application. Also, the strength of the affinity of the inorganic binding entity 101 for various substantially inorganic substances can be tuned by altering the number of residues (for example, the number of histidine or cysteine residues in a poly-histidine or poly-cysteine structure), the placement within a modular linker or the exact sequence of constituent residues, as desired.

As described in further detail below, another feature of the present invention is a general synthetic scheme for the simple and rapid synthesis of modular linkers of the present invention using solid phase peptide synthesis. For example, the entire linker may be synthesized from natural and unnatural amino acid and modified residue precursors, as desired. Alternatively, the entire linker or portions thereof may be synthesized entirely from non-peptidyl precursors and constituted from other molecules including, but not limited to, nucleotides, carbohydrates, lipids or may be almost completely non-biological in nature. Also, modular linkers provide an effective method for achieving stoichiometric control over the conjugation of an organic substance and a substantially inorganic substance, thus providing for homogeneous conjugation in a functionalized ratio without the occurrence of aggregates.

Thus, modular linkers of the present invention may be used to create functional substantially inorganic substance-organic substance constructs. When the substantially inorganic substances are nanomaterials and the organic substances are biomaterials, for example, modular linkers of the present invention may form the framework and an easy and cost effective method for constructing the next generation of usable hybrid bio-nanomaterials. For example, modular linkers provide a novel molecular framework that may be used for assembling fluorescent inorganic-biomaterial constructs useful for biosensing, drug delivery, optoelectronics, bionanotechnology, basic and applied research and other applications.

In other embodiments, the linker may be susceptible to chemical cleavage such that the inorganic and organic binding entities 101/103 may be separated when desired or in a particular environment. As a non-limiting example, a specific peptide sequence may be used as a spacer and provided as an optional entity 105/107. The presence of an appropriate protease will cleave the linker. In another non-limiting example, an ester may be used as an optional entity 105/107 in the linker such that esterases or non-specific hydrolysis will cleave the linker. Another non-limiting example is the use of a chemical group that is pH sensitive and is hydrolyzed at a particular pH.

An example of an application for a cleavable linker is as a therapeutic delivery agent, whereby, a substantially inorganic substance is a magnetic nanoparticle that can be directed to a target tissue through magnetic focusing and the organic substance is a therapeutic component, such as (but not limited to) a drug, antisense DNA, peptide, enzyme, etc. In such an application, the linker is preferably soluble, biocompatible and can get hydrolyzed, digested or otherwise broken or cleaved, for example in an intracellular environment, for releasing the therapeutic component.

Each entity 101/103 can be introduced as part of the synthesis process as desired to target a particular substantially inorganic substance and/or organic substance in a simple manner. For example, two modular linkers 100 may be synthesized with identical inorganic binding entities 101 but different organic binding entities 103, for example that target different functional groups. These two modular linkers 100, may be utilized in separate applications or, alternatively, to link two different organic substances to the same substantially inorganic substance, e.g. two different biomolecules bound to one QD. In another embodiment, a single modular linker 100 could include one inorganic binding entity 101 and two separate organic binding entities 103, of which one organic binding entity would be incorporated into the modular linker 100 as an optional entity 105. Thus, the optional entities 105/107, which may be provided in the linker 100 in any order, will provide any number and type of additional functional features to the modular linker 100. In alternative embodiments, one or more modular linkers 100 likewise may be synthesized to link two different substantially inorganic substances to the same organic substance via the use of two different inorganic binding entities 101 and one organic binding entity 103.

One of the advantages of the present invention is that the modular linker 100 can include an organic binding entity 103 having one of a variety of chemically reactive groups, such that a broad range of conjugation reactions are immediately available. For example, Table II provides a list of functionally reactive chemical groups to be provided as an organic binding entity 103 and of the portion of an associate organic substance that would be targeted by the functionally reactive chemical group. Thus, modular linkers are also functionally simple in their applications. When modular linkers are provided with the organic binding entity 103 in a reactive form, there is no need for multi-step conjugation reactions and/or multiple purification steps. Likewise, substantially inorganic substances and inorganic binding entities 101 relying on affinity for conjugation may be easily conjugated, for example through simple mixing in an appropriate buffer, with no need for complex binding chemistries.

Another advantage of the present invention is the synthetic simplicity of one or more modular linkers. The modular linkers of the present invention may be synthesized by any number of methods. For example, one method includes simple solid phase peptide synthesis (SPPS) in addition to simple SPPS modifications, as discussed in further detail below. Other methods include DNA synthesis or general chemical synthesis methods.

Further, a linker, once synthesized can be sold, transferred and stored in a reactive or non-reactive state at −20° C. Examples of modular linkers of the present invention have been stored at room temperature for up to 1 week and/or at −20° C. for more than 1 year, during which time the organic binding entity was still reactive. As such, a variety of modular linkers may be manufactured in large quantities, stored and commercially sold, for example as a research tool, either alone or as part of a conjugation kit. Further, the modular linkers can be stored by a commercial entity or by a researcher until such time as the modular linkers are required for use.

Another advantage of the modular linker of the present invention is that it imparts stoichiometric control. For example, mixing appropriate ratios of substantially inorganic substances and appropriate linker-organic substance constructs can result in inorganic substance-linker-organic substance constructs with precise desired organic substance to substantially inorganic substance ratios.

EXAMPLE 1

FIG. 2 is an example of a modular linker 200 for functionalizing certain substantially inorganic substance with a desired organic substance. In this example, inorganic binding entity 201 is a hexa-histidine $(His)_6$ peptidic tail, which is known to show an affinity for at least the surface of CdSe/ZnS QDs. Meanwhile, organic binding entity 203 is a functionally reactive chemical group covalently attached to the $(His)_6$ tail that has been selectively introduced to react with one or more target organic substances through a particular chemistry. FIG. 2 also demonstrates an optional entity 205 which is a spacer that is introduced to fine tune the conformational properties of the modular linker 200. In an alternative embodiment, optional entity 205 may be a chemical introduced to enhance the solubility of the modular linker 200 for various post-synthesis linker applications. The functionally reactive chemical group, designated X in FIG. 2, can be chosen from among many different functionally reactive chemical groups based on the most suitable conjugation chemistry for attachment to a desired target organic substance. See Table II for examples of functionally reactive chemical groups and the portions of organic substances that readily react therewith.

Thus, FIG. 2 demonstrates the modularity of the modular linker of the present invention in which one or more modular linkers may have a single inorganic binding entity 201 that is covalently bonded to different selected organic binding entities 203 depending upon the desired organic substance to be linked.

Figure 3:
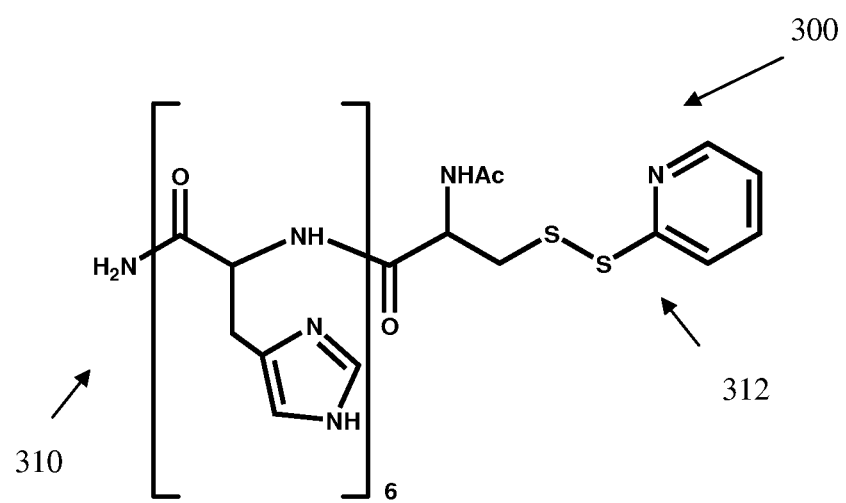
FIG. 3 is a structure of an example linker of the present invention including a hexa-histidine tail and terminating in a thiol reactive pyridyl disulfide.

FIG. 3 is an example of a modular linker 300 of the present invention. In FIG. 3, the modular linker 300 includes an organic binding entity, specifically the thiol of a cysteine, provided in the form of a reactive pyridyl-disulfide 312. The modular linker 300 also includes an inorganic binding entity, specifically a hexa-histidine tail 310 covalently bound to the reactive pyridyl-disulfide 312. Under appropriate reaction conditions, the modular linker 300 is capable of exploiting the well-known disulfide exchange reaction process, present in the reactive pyridyl-disulfide 312, for further conjugation to a thiol-modified organic substances, such as a thiolated nucleotide or other thiolated biomolecule, as would be apparent to one skilled in the art. The organic binding entity is not limited to a reactive pyridyl-disulfide 312, as demonstrated in FIG. 3, nor is the organic substance limited to one having a free thiol. Rather, an ample variety of conjugation chemistries may be easily adapted to the modular linker by simply introducing the appropriate functionally reactive chemical group. Since the $His_6$-Cys-SS-organic substance construct, facilitated by the modular linker 300 of FIG. 3, has demonstrated high affinity for the surface of CdSe/ZnS QDs, the use of a hexa-histidine tail and an appropriate functionally reactive chemical group may allow for the controlled conjugation of CdSe/ZnS QDs with virtually any organic substance or any biomolecule.

EXAMPLE 2

Figure 4:
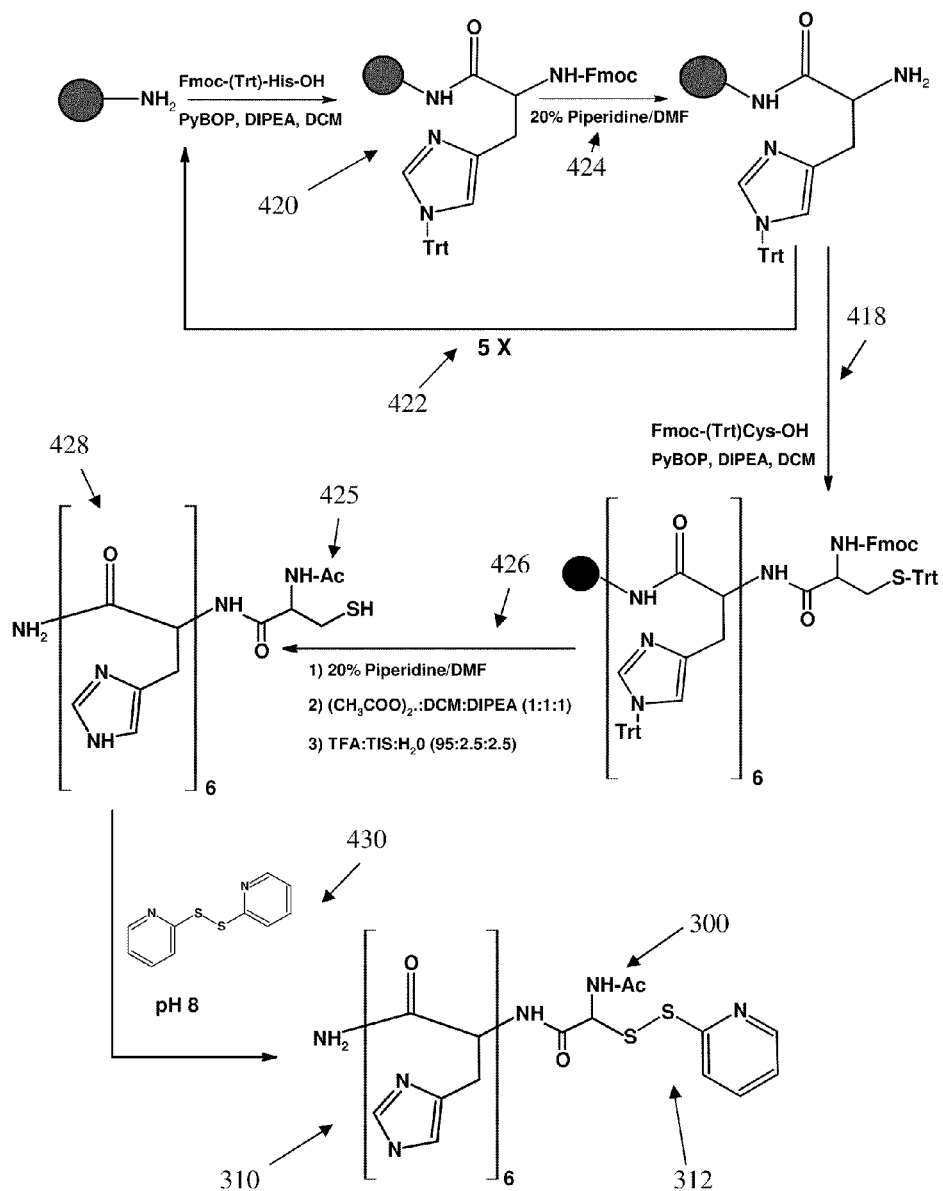
FIG. 4 is a scheme for synthesizing the example of a linker of FIG. 3.

FIG. 4 illustrates the general synthetic scheme 418 for the standard solid phase peptide synthesis (SPPS) of the modular linker 300 of FIG. 3 having a $(His)_6$-tail 310 terminating in a reactive residue, particularly a reactive pyridyl-disulfide 312, as an organic binding entity. In an alternative synthetic scheme, the inorganic binding entity, i.e., the $(His)_6$-tail 310 in the example of FIG. 4, may be synthesized using any natural or unnatural amino acid sequence or other appropriate precursor molecules using similar well known SPPS, as would be apparent to one skilled in the art. For example, several other peptidyl sequences are discussed above that are known to provide affinity for various substantially inorganic substances. Any of these peptidyl sequences can be synthesized from amino acids or other appropriate precursor molecules using the SPPS procedure identified in FIG. 4. Further, a post-SPPS step can be executed upon peptide cleavage from the resin, to modify further the reactive terminal residue.

The standard SPPS, which would be apparent to one skilled in the art, was started by attaching the first 9-fluorenyl-methoxycarbonyl-histidine residue (Fmoc-His) to Rink amide polystyrene resin, forming the first histidine of the $(His)_6$ chain 420. The Fmoc-His was activated with PyBOP, and the reaction was conducted in dichloromethane (DCM) in the presence of diisopropylethylamine (DIPEA). The remaining residues were introduced similarly by cyclically repeating 422 the steps and removing the Fmoc amino-protective group at each step by treatment with 20% Piperidine in dimethylformamide (DMF) 424.

The terminal amine was then acylated by treatment with a 1:1:1 DCM:Acetic Anhydride:DIPEA mixture 426. The resin was then treated with a trifluoroacetic acid (TFA): triisopropyl silane (TIS):water (95:2.5:2.5) mixture, which resulted in both resin cleavage, resulting in a cysteine residue with a free thiol 425, and deprotection of the peptide side chains. The peptide was precipitated in cold diethyl ether, centrifuged, the supernatant removed and the pellet washed with cold diethyl ether. Finally, the pellet was resuspended in water with 0.1% TFA, and purified by reverse phase high performance liquid chromatography (HPLC). Post SPPS, a derivatization step was performed. In this case, the $(His)_6$-Cys-SH molecule 428 was then reacted with 2,2'-dipyridyldisulfide (ALDRITHIOL-2®) 430, resulting in a reactive modular linker 300 that is stable to oxidation. The excess 2,2'-dipyridyldisulfide 430 was then removed by reverse phase HPLC.

The modular linker of this example is demonstrated for exemplary purposes only. Methods other than SPPS may be used to synthesize a modular linker of the present invention, particularly those modular linkers that include inorganic binding entities that are not peptidyl sequences, as discussed above.

The synthesis of the $(His)_6$-tail is described in FIG. 4 and is carried out through standard SPPS. Upon cleavage and deprotection of the peptide, a further post-SPPS derivatization step, for example the reaction with 2,2'-dipyridyldisulfide, is used to complete the synthesis of a fully functional reactive modular linker. Alternatively, through the use of natural and unnatural amino acids during the SPPS, combined with the availability of commercial precursors and chemistries, modular linkers of the present invention are easily available in a broad range of chemical reactivities and chemical affinities. Some non-limiting examples of such reactivities are listed below in Table II, which illustrates various examples of functionally reactive chemical groups to be used as organic binding entities 103 and the portion of an organic substance that would be targeted by the functionally reactive chemical groups.

TABLE II

| Functionally Reactive Chemical Groups | Portion of an Organic Substance Targeted |
| --- | --- |
| Maleimide | Free Thiol |
| Haloacetyl derivatives | Free Thiol |
| Alkyl Halide derivatives | Free Thiol |
| Arylating agents | Free Thiol |
| Aziridine | Free Thiol |
| Acryloyl derivatives | Free Thiol |
| Pyridyl disulfides, TNB-thiol | Free Thiol |
| Hydrazine | Aldehyde |
| Amines | Aldehyde |
| NHS-ester | Free amine |
| Isocyanates, Isothiocyanates | Free amine |
| Acyl Azides | Free amine |
| Sulfonyl Chlorides | Free amine |
| Aldehydes | Free amine |
| Glioxals | Free amine |
| Epoxides | Free amine |
| Oxiranes | Free amine |
| Carbonates | Free amine |
| Arylating Agents | Free amine |
| Imidoesters | Free amine |
| Carbodiimides | Free amine |
| Anhydrides | Free amine |
| Diazoalkanes | Carboxylate |
| Diazoacetyl compounds | Carboxylate |
| Carbonyldiimidazole | Carboxylate |
| Carbodiimides | Carboxylate |
| Epoxides and Oxiranes | Hydroxyl |
| Cabonyldiimidazole | Hydroxyl |
| N,N'-disuccinimidyl carbonate | Hydroxyl |
| N-Hydrosuccinimidyl chloroformate | Hydroxyl |
| Periodate oxidation | Hydroxyl |
| Enzymatic oxidation | Hydroxyl |
| Alkyl Halogens | Hydroxyl |
| Isocyanates | Hydroxyl |
| Biotin | Streptavidin |

EXAMPLE 3

Figure 5:
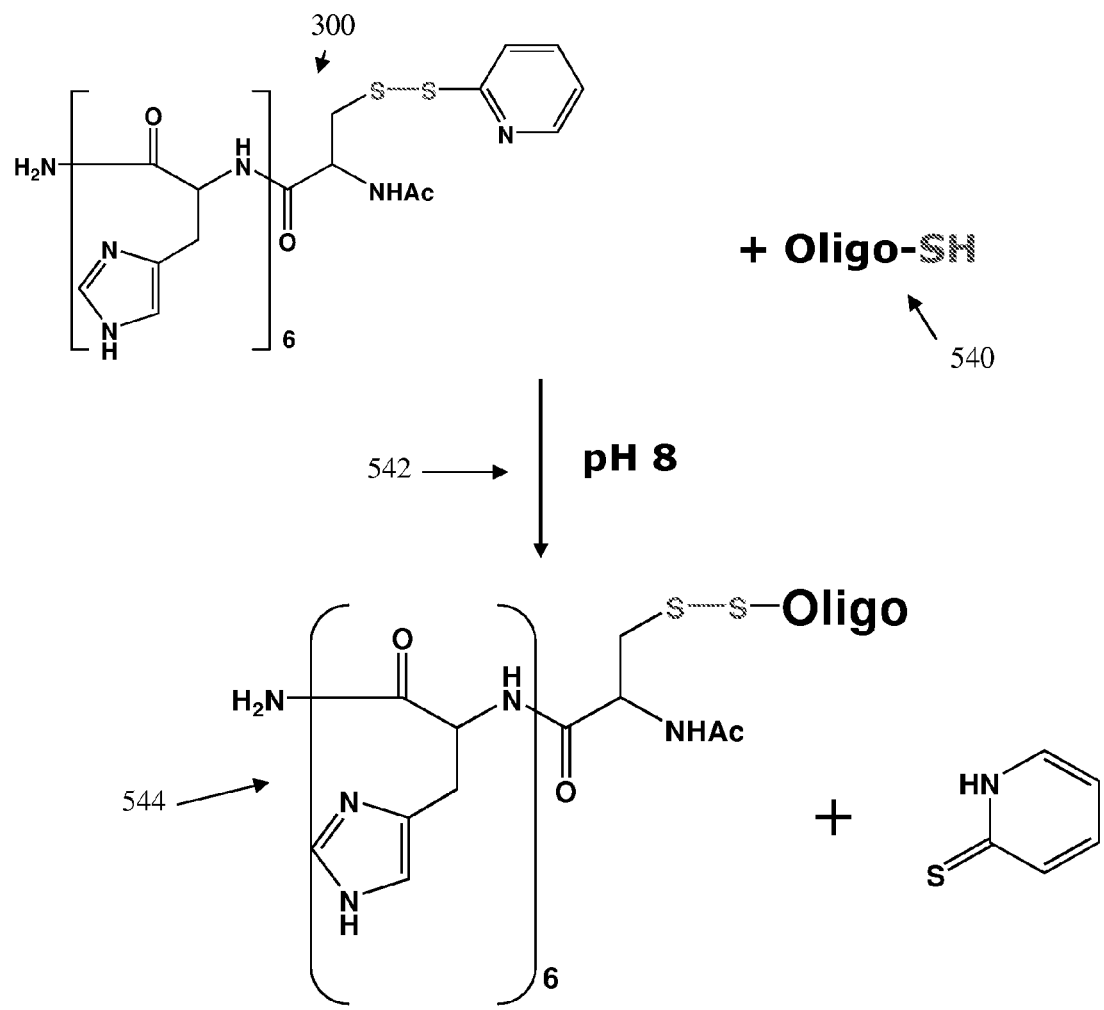
FIG. 5 is a scheme for coupling a thiolated-ssDNA with the example of a linker of FIG. 3.

FIG. 5 illustrates a schematic for coupling a thiolated-single stranded DNA (ssDNA) with the modular linker 300 of FIG. 3. A 3'-Thiol-modified ssDNA 540 was deprotected by treatment with dithiothreitol (DTT), the excess DTT removed by reverse phase HPLC or gel permeation chromatography, and immediately reacted with the $(His)_6$-Cys-SSPy linker 300 of FIG. 3. The reaction 542 was fast, and quantitative conjugation of the thiol-DNA was complete in about 30 min. The $(His)_6$-S—S-DNA construct 544 was purified by either reverse phase HPLC or gel filtration, for example on a pre-packed PD-10 cartridge.

EXAMPLE 4

Figure 6:
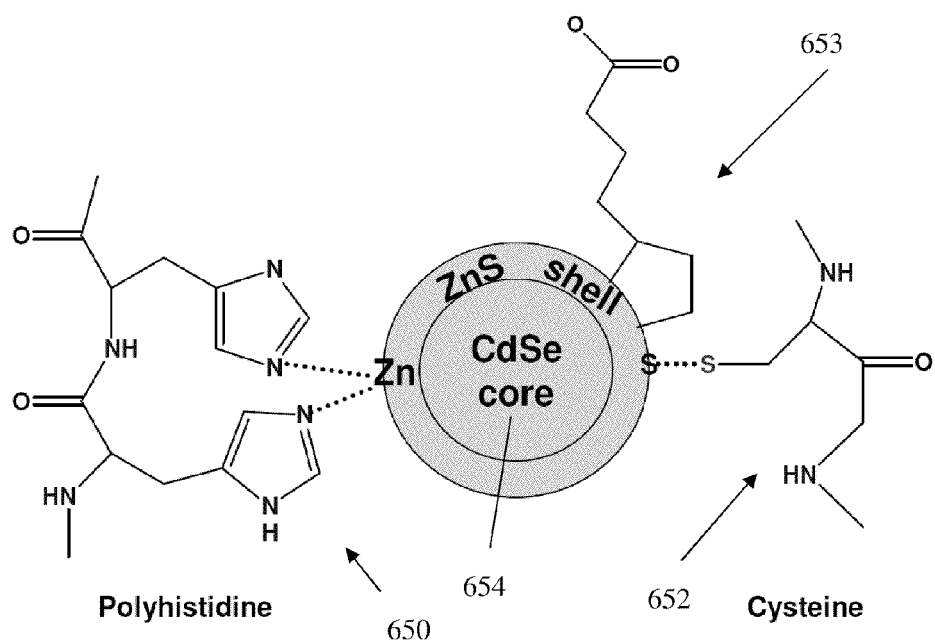
FIG. 6 is a schematic demonstrating the metal-affinity of poly-histidine residues and thiolated poly-cysteine residues for the surface of a CdSe/ZnS core/shell QD.

Further conjugation (not shown) of the $(His)_6$-S—S-DNA construct 544 to a substantially inorganic substance to which the $(His)_6$ portion has an affinity, here CdSe/ZnS QDs, was carried out by simply mixing both entities in buffer at the desired inorganic substance to DNA ratio to form a CdSe/ZnS QD-linker-DNA construct (not shown). FIG. 6 is a schematic demonstrating the metal-affinity of poly-histidine residues 650 and thiolated poly-cysteine residues 652 for the surface of a CdSe/ZnS QD 654. CdSe/ZnS QDs 654 may be previously treated with additional surface ligands, such as a dihydrolipoic acid 653, which provides solubility to the QD. A QD may be alternatively modified in any number of ways, including coating with a polymer layer and other modifications as would be apparent to one skilled in the art. Poly-histidine further demonstrates an affinity to other inorganic materials including, but not limited to, copper, cobalt, nickel, zinc, magnesium, iron and chromium. Similarly, poly-cysteine residues further demonstrate an affinity to other inorganic materials including, but not limited to gold, silver, sulfur, platinum, palladium, rhenium, cadmium, copper, ruthenium and mercury. Thus, the use of poly-histidine or poly-cysteine residues as the inorganic binding entity 101 does not limit the application to binding only to QDs.

EXAMPLE 5

Figure 7:
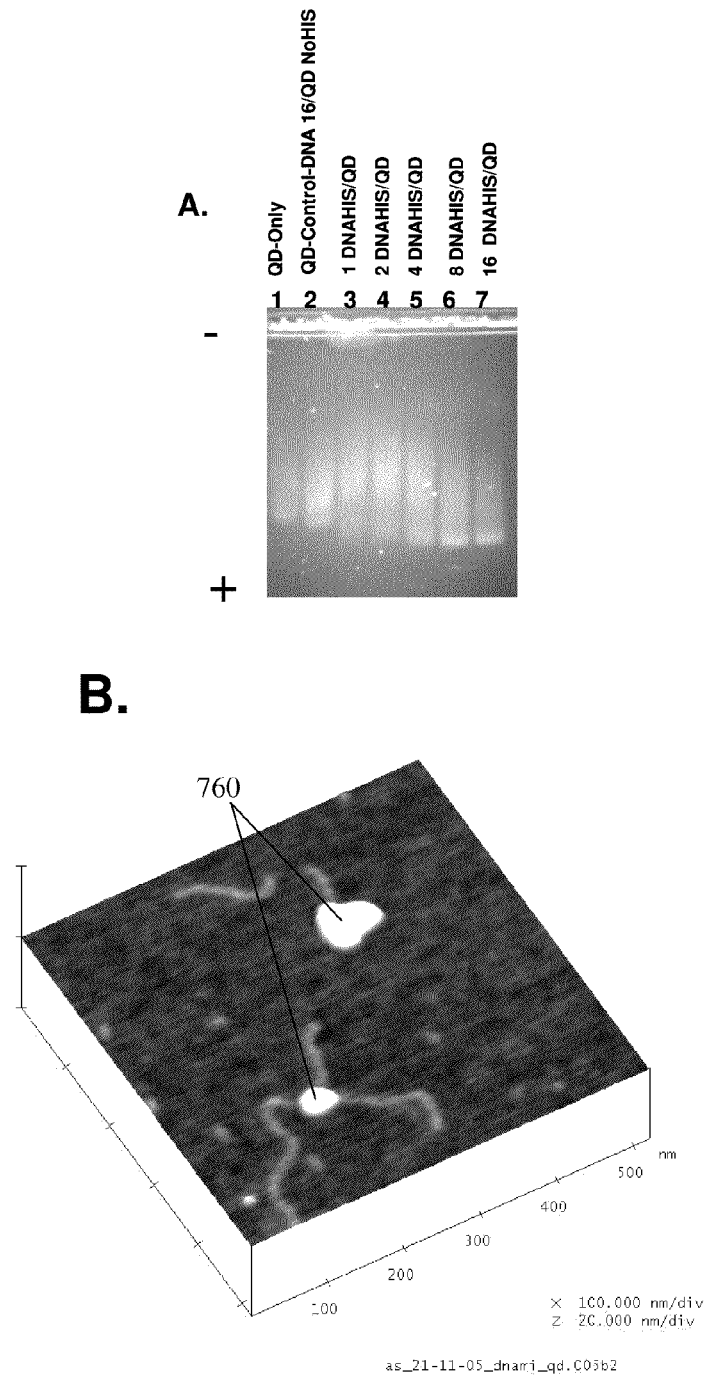
FIG. 7A is an agarose gel analysis demonstrating various stoichiometric ratios of DNA-poly-histidine modular linkers to QDs.
FIG. 7B is an atomic force microscopy image of DNA strands bound to QDs via a modular linker.

Proof of successful conjugation of the modular linker 300 with ssDNA 540 and dihydrolipoic acid treated CdSe/ZnS QDs 654 is demonstrated by running an agarose gel electrophoresis. FIG. 7A is an agarose electrophoresis gel analysis of dihydrolipoic acid treated CdSe/ZnS QDs functionalized with various stoichiometric ratios of $(His)_6$-Cys-ssDNA constructs 544. Individual lanes of the gel are labeled and numbered at the top of the gel. Increasing the number of the $(His)_6$-Cys-ssDNA constructs 544 bound to each QD 654 increases their mobility in the gel by increasing the charge of the molecules. However, the mobility appears to plateau around a ratio of 8 $(His)_6$-Cys-ssDNA constructs 544 per QD 654. QDs mixed with an equivalent of 16 control thiolated DNA but lacking the modular linker, here $(His)_6$-Cys-ss, migrated at the same rate as QDs alone, thus demonstrating that the QDs were not bound to the ssDNA without the use of the linker.

FIG. 7B is an Atomic Force Microscopy (AFM) image demonstrating the QD-linker-DNA constructs after the DNA was further hybridized with a longer, so as to be observable, DNA strand. The QD-DNA construct 760 was placed on mica in order to observe the attachment of the DNA to the QDs.

The reactivity of the modular linker towards a targeted biomolecule is introduced through a functionally reactive chemical group at the organic binding entity 103. The chemical reactivity or affinity of the organic binding entity 103 allows the chemical conjugation of the organic binding entity 103 to a number of appropriately functionalized organic substances, including DNA and other modified oligonucleotides, proteins, peptides, enzymes, antibodies and other protein targets, carbohydrates, sugars, lipids, other biomolecules or even completely non-biological organic substances, such as alkane chains. The targeting to a different organic substance may be achieved by selecting the appropriate functionally reactive chemical group of the organic binding entity 103. For example, the functionally reactive chemical group may be selected from a reactive maleimide group that targets thiols of organic substances, a reactive NHS-ester group that targets primary amines of organic substances, or a variety of targets of organic substances. See Table II for other additional examples of functionally reactive chemical groups and their respective organic substance targets.

The $(His)_6$-tail 310 of modular linker 300 shows great affinity for the surface of CdSe/ZnS QDs 654, allowing for sequential introduction of a modular linker having the $(His)_6$-tail 310 onto the QD and stoichiometric control over the QD to linker or QD to organic substance ratio. Upon conjugation to a target of an organic substance, the $(His)_6$-tail recognizes and binds the surface of a CdSe/ZnS QD.

A modular linker of the present invention may be useful in a variety of applications, as would be apparent to one skilled in the art. One application of this invention includes, for example, the sale and use in all areas where fluorescent detection of organic substances is required. These include, but are not limited to, the following areas: biosensing, medical diagnostics, drug detection and drug candidate screening, as well as both qualitative and quantitative bio-analysis in tethered and soluble assay formats. Another example of an application is as a ready-made reactive linker as part of a conjugation kit for binding, conjugating, coordinating and/or attaching any targeted organic substance to an appropriate substantially inorganic substance. The design of modular linker of the present invention is such that use of the appropriate inorganic and organic binding entities 101/103 will facilitate the conjugations of almost any targeted organic substance to a variety of substantially inorganic substances, even if the substantially inorganic substance or organic substance are appropriately modified for such a purpose where necessary, for example, a thiolated DNA sequence or a treated QD for enhanced solubility.

EXAMPLE 6

For example, a fluorescent QD-linker-oligonucleotide construct may be assembled through a modular linker of the present invention. The fluorescent QD-linker-oligonucleotide construct may consist, for example, of two fluorescently labeled molecules interacting with each other through Fluorescence Resonance Energy Transfer (FRET). As would be apparent to one skilled in the art, FRET includes a change in measurable fluorescence via energy transfer between two molecules, one a donor molecule and one an acceptor molecule, by binding the two molecules in close proximity. The two fluorescent entities may be linked, for example, via a modular linker of the present invention to retain the close proximity needed for energy transfer. In this example, the $(His)_6$-Cys-SS-Py linker of FIG. 3 is synthesized separately, as discussed above. A thiol-modified and fluorescent dye labeled ssDNA is the acceptor of the FRET system while the donor consists of a CdSe/ZnS QDs. The modular linker 300 keeps the labeled ssDNA and the QD in close proximity such that energy transfer can occur between the two molecules.

Specifically, disulfide exchange between the thiol-ssDNA and the pyridyl disulfide results in a quantitative (His)$_6$-Cys-SS-dye labeled ssDNA construct. Simply mixing the (His)$_6$-Cys-SS-dye labeled ssDNA construct with CdSe/ZnS QDs at a desired ratio results in self assembly of the desired FRET system by creating a QD-(His)$_6$-Cys-SS-dye labeled ssDNA construct, keeping the QD and the labeled ssDNA construct in close proximity.

Figure 8:
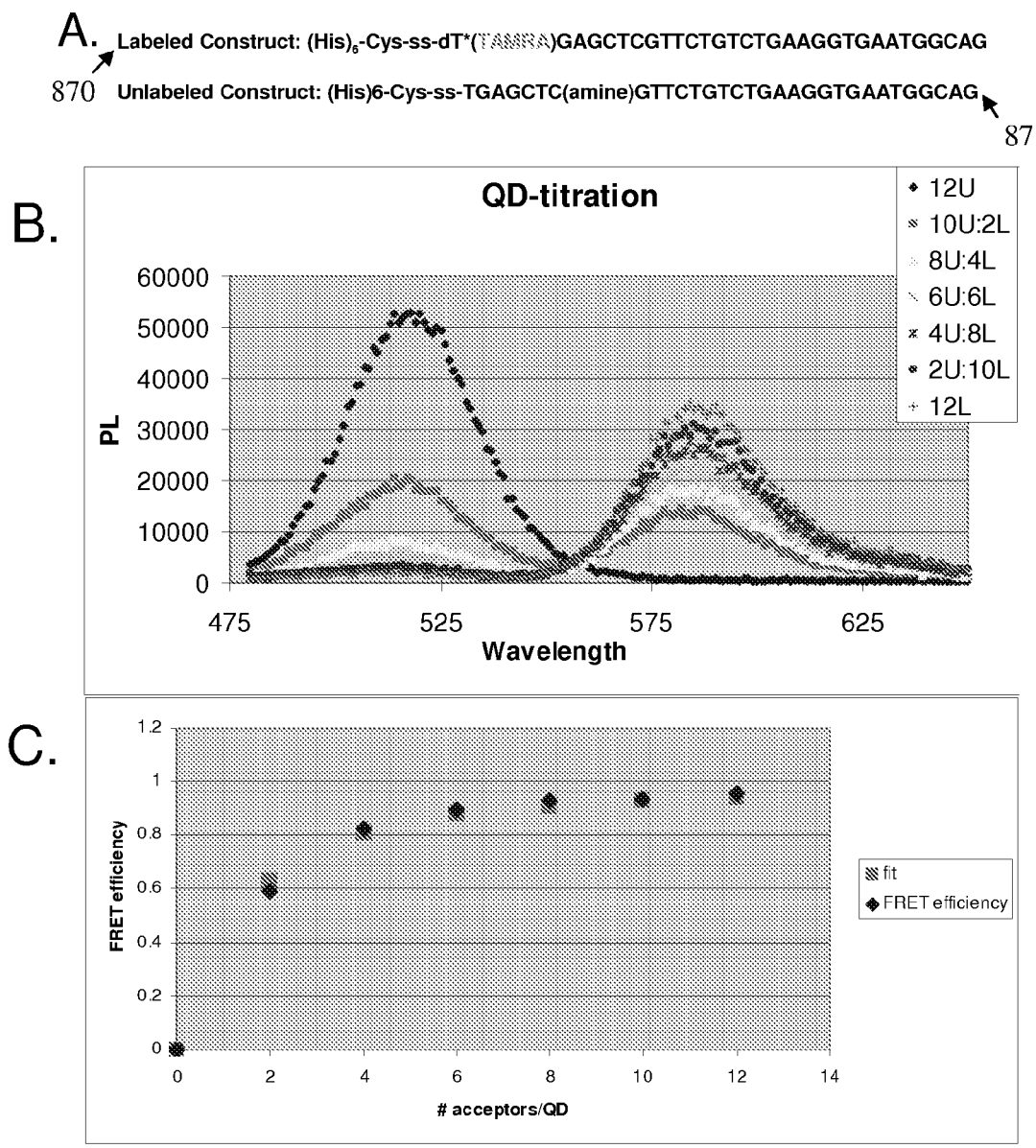
FIG. 8A are two modular linker-DNA constructs that include modified DNA sequences, including one labeled for fluorescence resonance energy transfer (FRET) based experiments and one unlabeled that includes an introduced non-labeled amine which is used as a control for FRET based experiments.
FIG. 8B illustrates a resultant spectra from a titration of QDs functionalized with different ratios of the labeled (L) and unlabeled (U) modular linker-DNA constructs of FIG. 8A, illustrating an increase in resonance-energy transfer with an increase in ratio of labeled modular linker-DNA constructs per QD.
FIG. 8C is a comparison of measured FRET efficiency with a theoretical calculated efficiency, demonstrating effective energy transfer achieved using a modular linker of the present invention to facilitate self-assembly of the labeled DNA to the QD surface.

FIG. 8A are examples of two sequences of modular linker-DNA constructs that include modified DNA used for a FRET based experiments given 5'-3', left to right. The modular linker-labeled DNA construct 870 contains a modified DNA molecule having an internal tetra-methyl rhodamine (TAMRA) dye, suitable for FRET with these emitting QD donors. The control modular linker-unlabeled DNA construct 871 is essentially identical except that the DNA molecule is modified to include an internal amine, which does not carry the fluorescent dye label, and is thus unsuitable for FRET. FIG. 8B illustrates a resultant spectra from a titration of QDs functionalized with different ratios of labeled (L) and unlabeled (U) modular linker-DNA constructs 870/871. Of note is the dramatic increase in photoluminescence (PL) at the longer wavelength as the ratio of QD-(His)$_6$-Cys-SS-acceptor dye labeled ssDNA constructs increases, illustrating that the QD and the labeled ssDNA are in close enough proximity to exhibit energy transfer to the longer wavelength. Thus, the increase in ratio of labeled DNA to non-labeled DNA increases the efficiency of donor energy transfer, demonstrated by the significant loss of PL from the QD donor at a wavelength of about 520 nanometers.

FIG. 8C is a comparison of the theoretical FRET efficiency (fit) with the experimentally demonstrated FRET efficiency, as derived from the loss in photoluminescence at the smaller wavelength, calculated using Foster formalism, as would be apparent to one skilled in the art. As demonstrated by FIG. 8C, the experimental efficiency nearly matches the expected efficiency showing that the linker of the present invention may be used successfully in FRET labeling applications.

EXAMPLE 7

The (His)$_6$-Cys-SS-Py linker 300 of FIG. 3 was synthesized, as discussed above. The modular linker of FIG. 3 was stored from several days up to one year at −20° C. without any loss of activity of the pyridyl disulfide. Further, the modular linker has a shelf-life at ambient temperature from a day up to at least one week. For example, the modular linker of FIG. 3 was successfully transferred from Bologna, Italy to Washington, D.C. at ambient temperature without a loss of activity of the pyridyl disulfide over about a 1 week time frame. It is believed that the modular linker of the present invention is stored and transferred easily in a stable condition anytime from a day to a week to a year without a loss of activity. In other words, a modular linker of the present invention may have a shelf-life ranging from about a day to up to a year.

While the invention has been particularly shown and described with reference to preferred embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents. Additionally, all references cited herein, including issued U.S. patents, or any other references, are each entirely incorporated by reference herein, including all data, tables, figures, and text presented in the cited references. Also, it is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein.

What is claimed as new and desired to be protected by Letters Patent of the United States is:

1. A modular linker, comprising:
   (a) an inorganic binding entity having an affinity for a substantially inorganic substance; and
   (b) an organic binding entity capable of binding with an organic substance, wherein the organic binding entity is covalently bonded to the inorganic binding entity, and wherein the modular linker is capable of being stored in a stable condition for later use; and
   wherein the inorganic binding entity is a polypeptide sequence selected from the group consisting of a poly-histidine sequence, a poly-cysteine sequence and SEQ ID NOS 1-28.

2. The modular linker of claim 1, wherein the modular linker is stored in a stable condition in an inert environment.

3. The modular linker of claim 1, wherein the organic binding entity is in a reactive state and the modular linker has a shelf-life for about a day up to at least 1 week at ambient temperature without compromising the activity of the organic binding entity.

4. The modular linker of claim 1, the organic binding entity is in a reactive state and the modular linker has a shelf-life of about a day up to at least 1 year at about −20° C. without compromising the activity of the organic binding entity.

5. The modular linker of claim 1, wherein the organic binding entity is selected from the group consisting of a functional chemical group selective to a particular region of a biomolecule, an aptamer selective to a specific protein, a biotin selective to avidin, a glucose molecule selective to a glucose binding protein, a sugar selective to lectin, an antigen or hapten selective to a particular antibody, antibody selective to a particular antigen or hapten, p-benzylguanine modified group selective to DNA alkyl transferase, glutathione selective to glutathione-s-transferase, and a nucleotide sequence selective to a complementary nucleotide sequence.

6. The modular linker of claim 1, wherein said organic binding entity is a biomolecule binding entity capable of binding with a biomolecule.

7. The modular linker of claim 1, further comprising a spacer covalently bonded between the inorganic binding entity and the organic binding entity.

8. The modular linker of claim 7, wherein the spacer is susceptible to chemical cleavage in predetermine conditions.

9. The modular linker of claim 7, wherein the spacer is selected from the group consisting of a peptidyl sequence, a nucleotide sequence, an alkane chain, a chemical polymer of a predetermined length, a block copolymer, a hydroxylated compound and a lipid.

10. The modular linker of claim 1, further comprising an additional entity, wherein the additional entity is one that modulates the solubility of the chemical linker.

11. The modular linker of claim 10, wherein the additional entity is selected from a group consisting of a hydroxylated compound, a sugar, an oligosaccharide, a charged peptidyl residue and a sulfonated chemical group.

12. The modular liner of claim 10, wherein the additional entity is covalently bonded between the inorganic binding entity and the biomolecule binding entity.

13. The modular linker of claim 10, wherein the additional entity is covalently bonded to at least one of the inorganic binding entity and the biomolecule binding entity.

14. The modular linker of claim 1, further comprising an additional conjugation entity that includes attachment points capable of binding to alternative substrates.

15. The modular linker of claim 1, wherein the organic binding entity is reactive.

16. The modular linker of claim 1, further comprising a fluorescence encoded organic substance bound to the organic binding entity.

17. The modular linker of claim 1, wherein the substantially inorganic substance is a quantum dot or nanocrystal.

18. The modular linker of claim 1, wherein one of the organic substance or the inorganic substance includes a donor for fluorescence resonance energy transfer that is capable of transferring resonance energy to the other of the organic substance or the inorganic substance when both the organic substance and the inorganic substance are conjugated to the modular linker.

19. A conjugation kit comprising the modular linker of claim 1.

20. The conjugation kit of claim 19, further comprising at least one reagent suitable for reacting the organic binding entity to an organic substance.

21. The conjugation kit of claim 19, further comprising at least one buffer suitable for use in conjugating the inorganic binding entity to a substantially inorganic substance.

22. A method for synthesizing a stable modular linker, comprising:
  providing an inorganic binding entity having an affinity for a substantially inorganic substance;
    wherein the inorganic binding entity is a polypeptide sequence selected from the group consisting of a poly-histidine sequence, a poly-cysteine sequence and SEQ ID NOS 1-28;
  modifying the inorganic binding entity to be covalently bonded to an organic binding entity to form a modular linker; and
  storing the modular linker in an inert environment from about a day up to at least 1 week.

23. A method for linking a substantially inorganic substance to one or more organic substances, comprising:
  providing a modular linker having an inorganic binding entity having an affinity for the substantially inorganic substance; and an organic binding entity capable of reacting with at least one organic substance,
    wherein the organic binding entity is covalently bonded to the inorganic binding entity; and
    wherein the inorganic binding entity is a polypeptide sequence selected from the group consisting of a poly-histidine sequence, a poly-cysteine sequence and SEQ ID NOS 1-28;
  conjugating the modular linker to one or more organic substances by reacting the modular linker with at least one organic substance in substantially a 1:1 ratio; and
  conjugating the modular linker to a substantially inorganic substance by introducing the modular linker to the substantially inorganic substance in a suitable buffer in substantially a 1:1 ratio.

24. A modular linker, comprising:
(a) an inorganic binding entity having an affinity for a substantially inorganic substance; and
(b) a first organic binding entity capable of binding with a first organic substance and a second organic binding entity capable of binding with a second organic substance that is different from the first organic substance, wherein the first and second organic binding entities are covalently bonded to the inorganic binding entity;
  wherein the inorganic binding entity is a polypeptide sequence selected from the group consisting of a poly-histidine sequence, a poly-cysteine sequence and SEQ ID NOS 1-28.

25. A modular linker, comprising:
(a) a first inorganic binding entity having an affinity for a first substantially inorganic substance and a second inorganic binding entity having an affinity for a second substantially inorganic substance that is different from the first substantially inorganic substance; and
(b) an organic binding entity capable of binding with an organic substance, wherein the first and second inorganic binding entities are covalently bonded to the organic binding entity;
  wherein the first inorganic binding entity or the second inorganic binding entity is a polypeptide sequence selected from the group consisting of a poly-histidine sequence, a poly-cysteine sequence and SEQ ID NOS 1-28.

26. A modular linker, comprising:
(a) an inorganic binding entity having an affinity for a substantially inorganic substance; and
(b) an organic binding entity capable of binding with a nucleic acid sequence, wherein the organic binding entity is covalently bonded to the inorganic binding entity;
  wherein the inorganic binding entity is a polypeptide sequence selected from the group consisting of a poly-histidine sequence, a poly-cysteine sequence and SEQ ID NOS 1-28.

* * * * *